(12) United States Patent
Asnis et al.

(10) Patent No.: US 11,903,626 B2
(45) Date of Patent: Feb. 20, 2024

(54) FASTENER

(71) Applicants: The Feinstein Institute for Medical Research, Manhasset, NY (US); THE GENERAL HOSPITAL CORPORATION, Boston, MA (US)

(72) Inventors: Stanley E. Asnis, Great Neck, NY (US); Peter D. Asnis, Boston, MA (US)

(73) Assignees: THE GENERAL HOSPITAL CORPORATION, Boston, MA (US); THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 337 days.

(21) Appl. No.: 17/307,319

(22) Filed: May 4, 2021

(65) Prior Publication Data
US 2021/0322075 A1    Oct. 21, 2021

Related U.S. Application Data

(60) Continuation of application No. 16/274,452, filed on Feb. 13, 2019, now Pat. No. 11,026,731, which is a
(Continued)

(51) Int. Cl.
*A61B 17/86*    (2006.01)
*A61F 2/08*     (2006.01)

(52) U.S. Cl.
CPC ........ *A61B 17/863* (2013.01); *A61B 17/8645* (2013.01); *A61F 2/0811* (2013.01);
(Continued)

(58) Field of Classification Search
None
See application file for complete search history.

(56) References Cited

U.S. PATENT DOCUMENTS

| 6,162,234 A | 12/2000 | Freedland et al. |
| 6,436,139 B1 * | 8/2002 | Shapiro .................. A61F 2/446 |
| | | 623/17.11 |
| 2012/0203340 A1 | 8/2012 | Choinski et al. |

FOREIGN PATENT DOCUMENTS

| EP | 0651979 A1 | 5/1995 |
| EP | 0714643 A1 | 6/1996 |
| EP | 2298183 A1 | 3/2011 |

OTHER PUBLICATIONS

PCT International Search Report and Written Opinion, dated Mar. 4, 2014, pp. 1-14.

* cited by examiner

*Primary Examiner* — Sameh R Boles
(74) *Attorney, Agent, or Firm* — TAROLLI, SUNDHEIM, COVELL & TUMMINO L.L.P.

(57) ABSTRACT

A fastener includes an elongate fastener body defining a longitudinal axis substantially central thereto. The fastener body has a continuous outer fastener shell laterally surrounding the longitudinal axis. The fastener shell longitudinally separates a fastener head end and a fastener tip end. A tool-engaging feature is provided on the fastener head end. A plurality of teeth are located on the fastener shell and extend substantially laterally outward from the longitudinally axis. The fastener shell is comprised of at least one undulate face and at least one substantially flat face. The plurality of teeth are located only on the undulate faces. Each tooth is longitudinally separated from adjacent teeth along an undulate face. A method of installing the fastener into a receiving structure is also described.

5 Claims, 13 Drawing Sheets

Related U.S. Application Data division of application No. 14/146,347, filed on Jan. 2, 2014, now Pat. No. 10,238,440.

(60) Provisional application No. 61/748,788, filed on Jan. 4, 2013.

(52) U.S. Cl.
CPC ....... *A61B 17/8625* (2013.01); *A61B 17/8685* (2013.01); *A61F 2002/0852* (2013.01); *A61F 2002/0882* (2013.01)

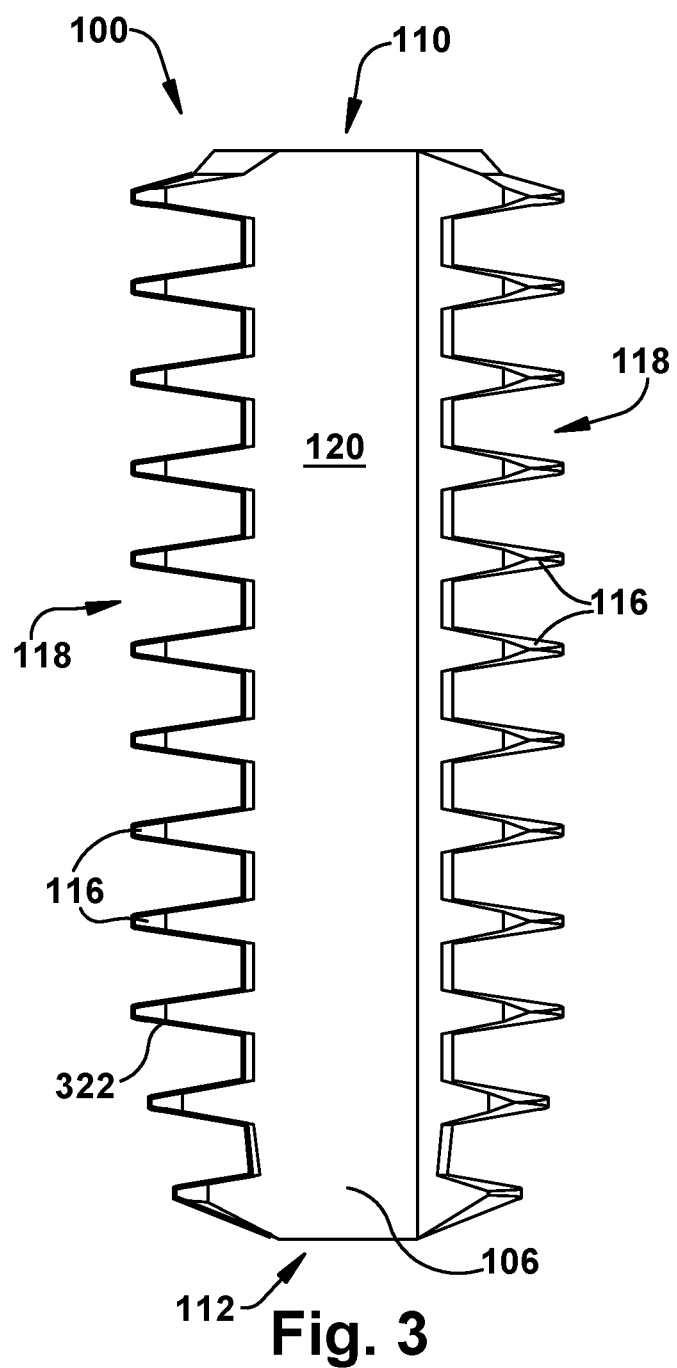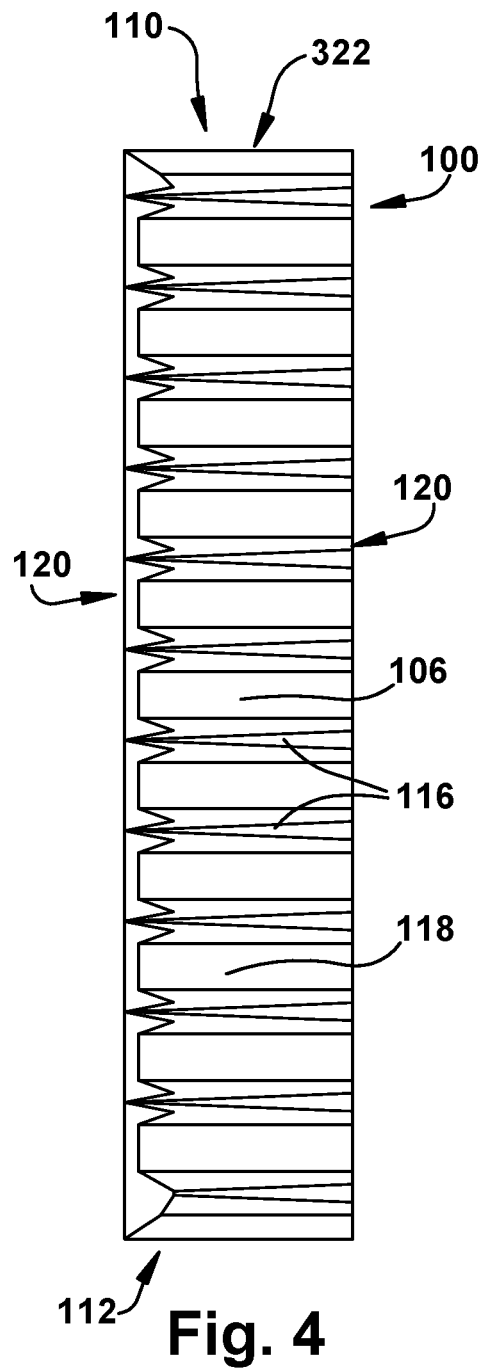

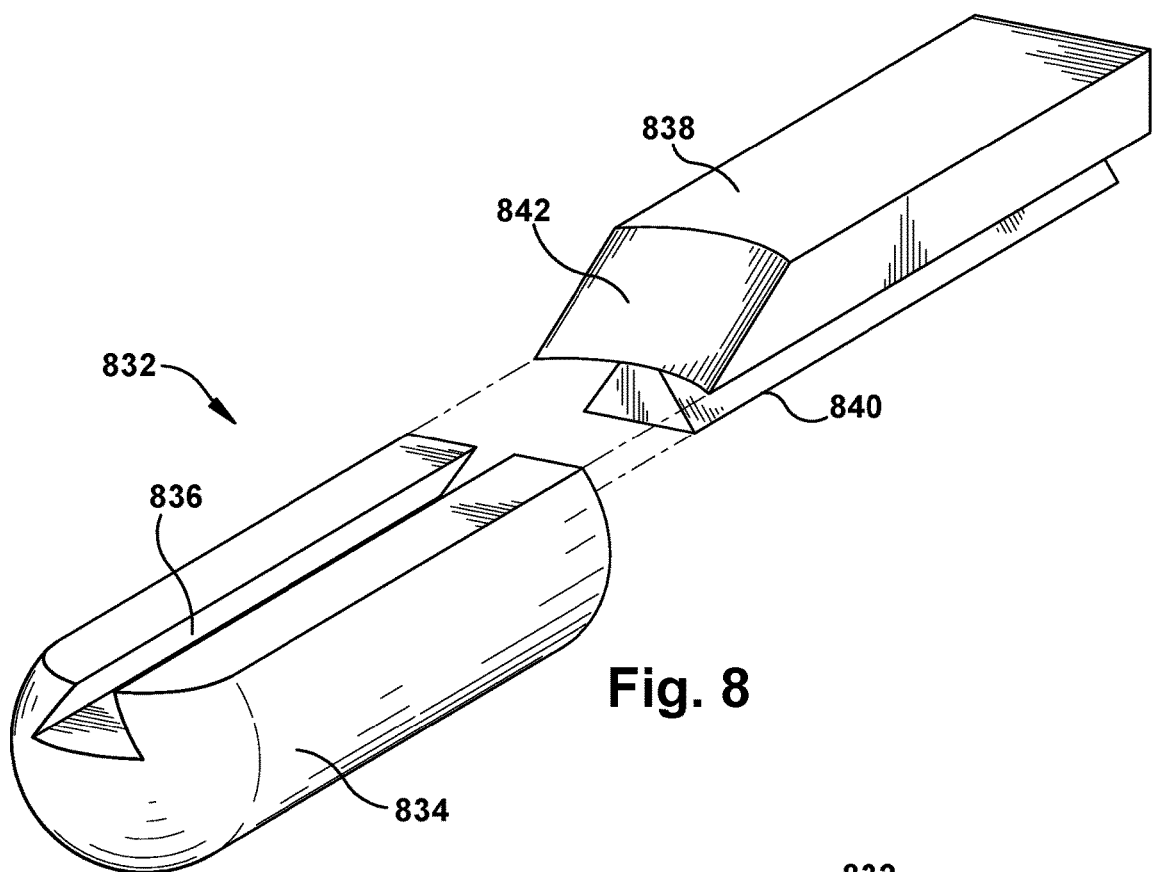
Fig. 8
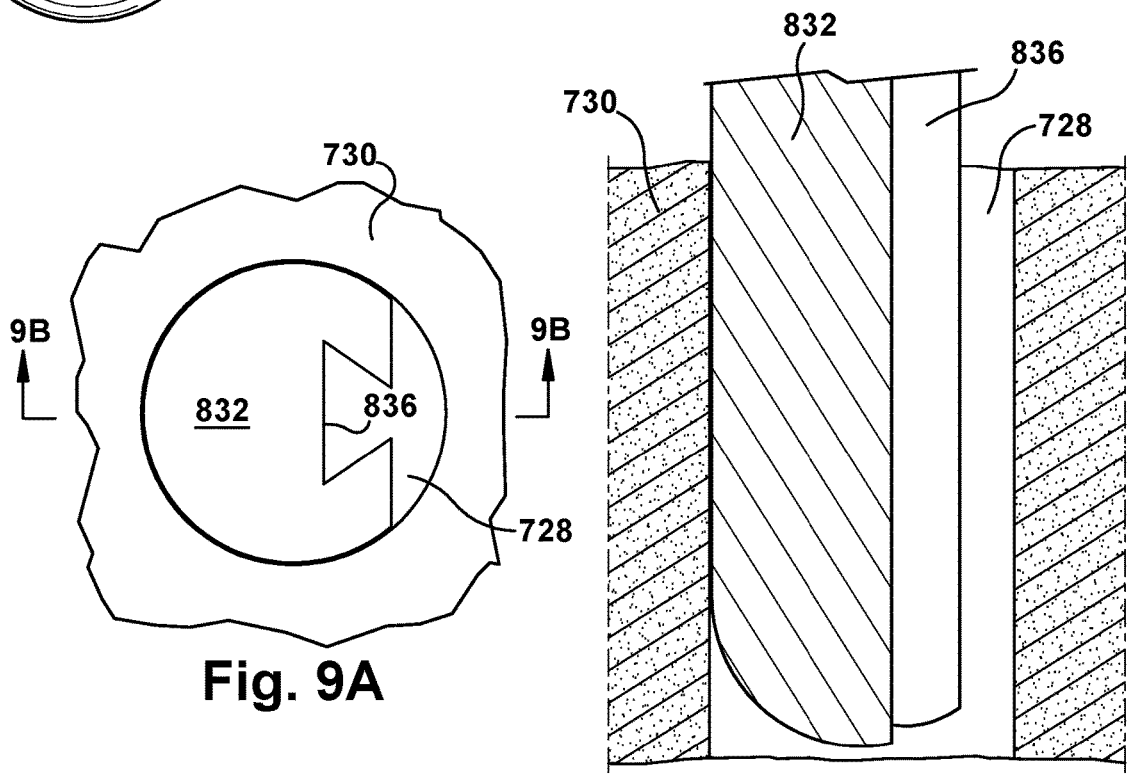
Fig. 9A
Fig. 9B

FASTENER

RELATED APPLICATION

This application is a continuation of U.S. patent application Ser. No. 16/274,452, filed Feb. 13, 2019, which is a divisional application of U.S. patent application Ser. No. 14/146,347, filed Jan. 2, 2014, now U.S. Pat. No. 10,238,440, which claims priority from U.S. Provisional Application No. 61/748,788, filed 4 Jan. 2013. Each of the aforementioned applications is incorporated herein by reference in its entirety.

TECHNICAL FIELD

The present invention relates to an apparatus and method for use of a fastener and, more particularly, to a fastener and method of installing a fastener into a receiving structure.

BACKGROUND OF THE INVENTION

Ligaments are tough bands of tissue which serve to connect the articular extremities of bones, or to support or retain organs in place within the body. Ligaments are typically composed of coarse bundles of dense white fibrous tissue which are disposed in a parallel or closely interlaced manner, with the fibrous tissue being pliant and flexible, but not significantly extensible.

In many cases, ligaments are torn or ruptured as a result of accidents. As a result, various procedures have been developed to repair or replace such damaged ligaments.

For example, in the human knee, the anterior and posterior cruciate ligaments ("ACL" and "PCL") extend between the top end of the tibia and the bottom end of the femur. The ACL and PCL cooperate, together with other ligaments and soft tissue, to provide both static and dynamic stability to the knee. Often, the ACL is ruptured or torn as a result of, for example, a sports-related injury. Consequently, various surgical procedures have been developed for reconstructing the ACL so as to restore normal function to the knee.

In many instances, the ACL may be reconstructed by replacing the ruptured ACL with a graft ligament. More particularly, with such procedures, bone tunnels are typically formed in the top end of the tibia and the bottom end of the femur, with one end of the graft ligament being positioned in the femoral tunnel and the other end of the graft ligament being positioned in the tibial tunnel. The two ends of the graft ligament are anchored in place so that the graft ligament extends between the femur and the tibia in substantially the same way, and with substantially the same function, as the original ACL. This graft ligament then cooperates with the surrounding anatomical structures so as to restore normal function to the knee.

In some circumstances the graft ligament may be a ligament or tendon which is harvested from elsewhere in the patient; in other circumstances the graft ligament may be a synthetic device. For the purposes of the present invention, all of the foregoing can be collectively referred to as a "graft ligament". A "bone graft", made of a denser/firmer material than the relatively soft-tissue graft ligament, may be provided at one or both ends of the graft ligament to assist with anchoring the graft ligament. When present, the bone graft, optionally along with a portion of the graft ligament, may be inserted into a bone tunnel previously machined into the tibia or femur, to assist with secure anchoring of the graft ligament.

SUMMARY OF THE INVENTION

In an embodiment of the present invention, a fastener is described. An elongate fastener body defines a longitudinal axis substantially central thereto. The fastener body has a continuous outer fastener shell laterally surrounding the longitudinal axis. The fastener shell longitudinally separates a fastener head end and a fastener tip end. A tool-engaging feature is provided on the fastener head end. A plurality of teeth are located on the fastener shell and extend substantially laterally outward from the longitudinally axis. The fastener shell is comprised of at least one undulate face and at least one substantially flat face. The plurality of teeth are located only on the undulate faces. Each tooth is longitudinally separated from adjacent teeth along an undulate face.

In an embodiment of the present invention, a method of installing a fastener into a receiving structure is described. A fastener is provided. The fastener includes an elongate fastener body, having longitudinally spaced fastener head and fastener tip ends. The fastener body defines a longitudinal axis. Two elongate flat faces are provided, each flat face extending substantially parallel to, and laterally spaced from, the longitudinal axis. The two flat faces are located laterally opposite one another on the fastener body. Two elongate undulate faces are provided, each undulate face having a plurality of longitudinally spaced teeth arranged thereupon. Each undulate face extends substantially parallel to, and is laterally spaced from, the longitudinal axis. The two undulate faces are located laterally opposite one another on the fastener body. The two undulate faces are laterally separated from one another by interposed flat faces. A fastener perimeter is defined in a lateral plane by the two flat faces and the two undulate faces. The fastener perimeter entirely laterally surrounds the longitudinal axis. A longitudinally oriented receiving aperture is provided in the receiving structure. The fastener tip end is inserted into the receiving aperture. The receiving aperture is penetrated with the fastener body to a predetermined depth. The fastener is maintained in the receiving aperture in a first alignment. The fastener is rotated about the longitudinal axis within the receiving aperture into a second alignment. At least one tooth is driven laterally into the receiving structure from the receiving aperture due to rotation of the fastener into the second alignment. With the at least one tooth driven laterally into the substrate, the fastener is maintained in the receiving aperture in the second alignment to resist longitudinal movement of the fastener with respect to the receiving aperture.

In an embodiment of the present invention, a fastener is described. An elongate fastener body has longitudinally spaced fastener head and fastener tip ends. The fastener body defines a longitudinal axis. Two elongate flat faces are provided, each flat face extending substantially parallel to, and laterally spaced from, the longitudinal axis. The two flat faces are located laterally opposite one another on the fastener body. Two elongate undulate faces are provided. Each undulate face has a plurality of longitudinally spaced teeth arranged thereupon, each undulate face extending substantially parallel to, and laterally spaced from, the longitudinal axis, the two undulate faces being located laterally opposite one another on the fastener body, and the two undulate faces being laterally separated from one another by interposed flat faces;

wherein a fastener perimeter is defined in a lateral plane by the two flat faces and the two undulate faces, the fastener perimeter entirely laterally surrounding the longitudinal axis.

BRIEF DESCRIPTION OF THE DRAWINGS

For a better understanding of the invention, reference may be made to the accompanying drawings, in which:

FIG. 3 is a front view of the embodiment of FIG. 1;

FIG. 4 is a side view of the embodiment of FIG. 1;

FIG. 8 is an exploded front perspective view of a tool which can be used with the use environment of FIG. 7A;

FIG. 9A is a top view of the tool of FIG. 8 in the use environment of FIG. 7A;

FIG. 9B is a cross-sectional view taken along line 9B-9B of FIG. 9A;

DESCRIPTION OF EMBODIMENTS

Figures 1, 2:
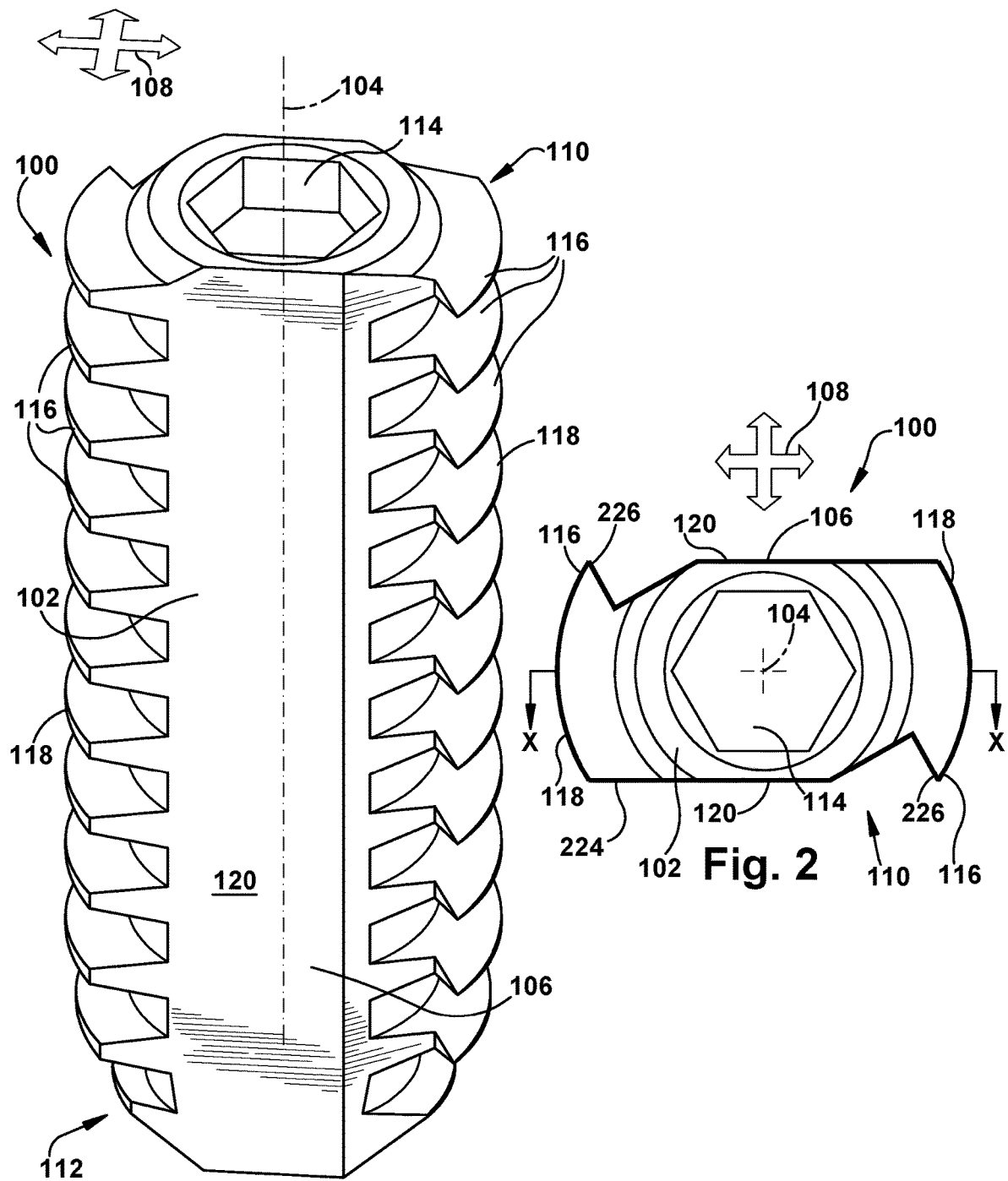
FIG. 1 is a perspective front view of an embodiment of the present invention.
FIG. 2 is a top view of the embodiment of FIG. 1.

In accordance with the present invention, FIGS. 1 and 2 depict a fastener 100. The fastener 100 includes an elongate fastener body 102 defining a longitudinal axis 104 substantially central thereto. The fastener body 102 has a continuous outer fastener shell 106 which laterally surrounds the longitudinal axis 104. A "lateral" direction 108, as described herein, is substantially located within or along a lateral plane which is substantially perpendicular to the longitudinal axis 104 (not restricted to the four arrowed "lateral" directions shown as examples in the Figures). The term "laterally surrounds" is used to indicate that a cross-sectional "slice" of the fastener shell 106 taken within a selected lateral plane completely encircles or encloses the portion of the longitudinal axis 104 located within that selected lateral plane.

The fastener shell 106 longitudinally separates a fastener head end 110 and a fastener tip end 112. The fastener head end 110 may include a tool-engaging feature 114, as will be discussed in more detail below. The fastener tip end 112 may be relatively tapered (i.e., have a smaller lateral cross-sectional footprint than the corresponding lateral cross-sectional footprint of a portion of the fastener body 102 closer to the fastener head end 110), even to a degree of taper to a relatively sharp point much like that of a commonly available wood screw. When tapered, the relatively smaller-diameter fastener tip end 112 may assist with orientation and/or location of the fastener 100 with respect to an existing receiving aperture and/or with a "self-tapping" function into a face of a substrate without a provided receiving aperture or with only a small "pilot hole" aperture.

A plurality of teeth 116 are located on the fastener shell 106 and extend substantially laterally outward from the longitudinal axis 104, though this lateral extension contemplates that one or more of the teeth 116 may be slightly tilted or canted with respect to a truly lateral orientation. Each of the teeth 116 may be of any desired construction, configuration, frequency, spacing, or have any other desired physical property, without regard to a corresponding physical property of other teeth of the fastener 100, and various contemplated options for the teeth will be discussed below in more detail. In the Figures, only a single tooth 116 or a small number of the total teeth 116 depicted may be called out with element numbers, for clarity of depiction, but one of ordinary skill in the art will understand that similar teeth would be numbered similarly.

The fastener shell 106 may be comprised of at least one undulate face 118 and at least one substantially flat face 120, as shown in FIG. 1. The "undulate" or "flat" nature of the face 118 or 120, respectively, may be determined by viewing it laterally (i.e., looking toward the longitudinal axis, as in the orientation of FIGS. 3-4). An "undulate" face 118 is one that has a wavy, crenellated, dentate, or other irregular surface, as opposed to a "flat" face 120, which is substantially planar but may include some incidental irregularities, such as the tooth 116 notches shown in FIG. 2. Stated differently, a cross-section of an undulate face 118 (e.g., a cross-section taken along a plane parallel to the longitudinal axis 104, such as along line x-x in FIG. 2) will include at least one peak and/or valley irregularity or departure from a base level. For example, FIG. 3 shows a side view of the fastener 100 with a profile 322 of one of the undulate faces 118 emphasized in heavy line. The undulate face 118 is shown straight-on in the side view of the fastener 100 in FIG. 4, with the peaks of the profile 322 extending out of the plane of the page toward the viewer, in that orientation.

Another way that the fastener 100 of FIGS. 1-2 can be characterized is as including at least two elongate flat faces 120, each extending substantially parallel to, and spaced laterally apart from, the longitudinal axis 104. The two flat faces 120 are located substantially laterally opposite one another on the fastener body 102. In the orientation of FIG. 2, the flat faces are toward the top and bottom of the page. Two elongate undulate faces 118 are provided, with each undulate face extending substantially parallel to, and laterally spaced from, the longitudinal axis 104. The two undulate faces 118 are located laterally opposite one another on the fastener body 102. The two undulate faces 118, which are located toward the left and right of the page in the orientation of FIG. 2, are laterally separated from one another by at least one interposed flat face 120, as shown. A fastener perimeter 224, shown in heavy line in FIG. 2, is defined in a lateral plane by the two flat faces 120 and two undulate faces 118. The fastener perimeter 224 entirely laterally surrounds the longitudinal axis 104.

In the embodiment shown in FIGS. 3 and 4, the profile 322 has a plurality of fairly sharp and regularly spaced "peaks" defined by the teeth 116. The plurality of teeth 116 are located only on the undulate faces 118. Each tooth 116 is longitudinally separated from longitudinally adjacent teeth along its respective undulate face 118. As shown in FIG. 4, each of the teeth 116 extends substantially across a lateral width (left to right in FIG. 4) of the undulate face 118. However, it is also contemplated that one or more teeth 116 could be located across only a portion of the lateral width of the undulate face 118, and that any such partial-width teeth (not shown) may be located at any desired location along the length or width of the undulate face 118, without regard to the location or configuration of other partial-width teeth that may be present.

Figures 5A, 5B, 5C:
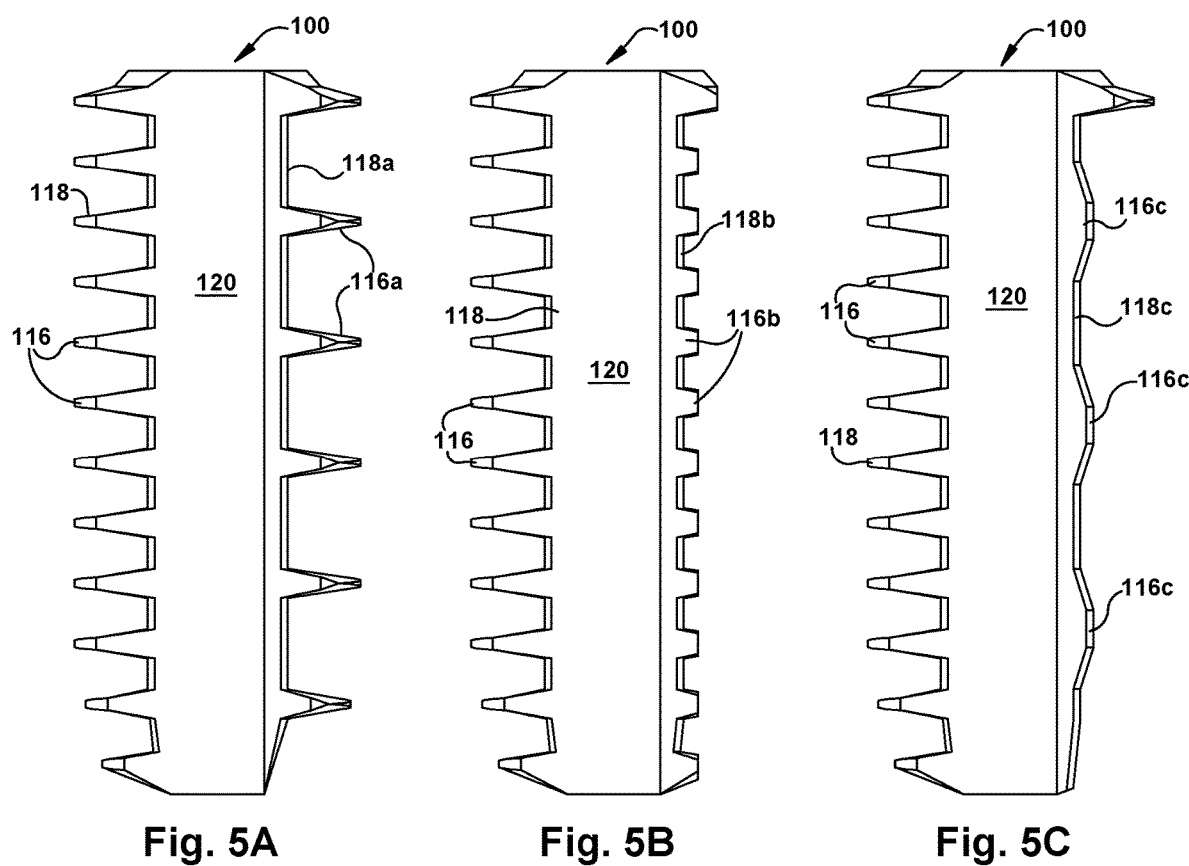
FIGS. 5A, 5B, and 5C are front views of alternate configurations of the embodiment of FIG. 1.

FIGS. 5A, 5B, and 5C each depict examples of configurations of undulate faces 118 that could be used with the present invention. In each of these Figures, the leftmost undulate face 118 is similar to those of FIGS. 3-4. In FIG. 5A, the rightmost undulate face 118a has a plurality of teeth 116a which have a similar configuration to, but different longitudinal spacing as, the teeth 116 on the leftmost undulate face 118. In FIG. 5B, the rightmost undulate face 118b has a plurality of teeth 116b which have similar longitudinal spacing to, but different configuration as, the teeth 116 on the leftmost undulate face 118b—the leftmost teeth 116b are significantly shorter than the rightmost teeth 116 in this embodiment. In FIG. 5C, the teeth 116c of the rightmost undulate face 118c are both fewer in number and smaller in "height" than the teeth 116 of the leftmost undulate face 116, with the teeth 116c also having relatively gentle, wavelike transitions along the longitudinal length of the rightmost undulate face 116. One of ordinary skill in the art can readily provide any number and configuration of suitable teeth 116, arranged along the undulate face(s) 118 in any desired manner, for a particular application of the present invention.

With reference back to FIG. 2, each tooth 116 of a selected undulate face 118 may include a leading edge apex 226 defined by a concave feature (here, the "check mark" shaped portions of the fastener perimeter 224) in a laterally oriented profile of the selected undulate face 118. The leading edge apex 226, when present, may cause the corresponding tooth 116 to be asymmetrical along the laterally oriented profile. In FIGS. 1 and 2, the leading edge apices 226 cause the teeth 116 of each undulate face 118 to be asymmetrical with respect to the line x-x. That is, when mirrored top-to-bottom along line x-x, the teeth 116 shown in FIGS. 1 and 2 are not symmetrical. When present, the leading edge apices 226 may be located on a portion of selected undulate face 118 (i.e., a "leading edge") that leads engagement of the tooth 116 with an ambient material when the fastener 100 is being rotated about the longitudinal axis 104.

Figure 6A:
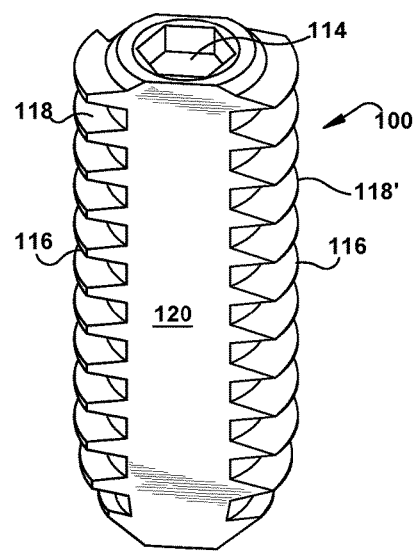
FIG. 6A is a perspective front view of an alternate configuration of the embodiment of FIG. 1.
Figure 6B:
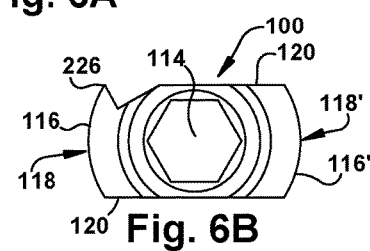
FIG. 6B is a top view of the embodiment of FIG. 6A.

In contrast, and with reference to FIGS. 6A and 6B, when a leading edge apex 226 is present, it is also contemplated that each tooth 116 of a second undulate face 118', other than the selected undulate face 118, is symmetrical along a laterally oriented profile of the second undulate face 118'. That is, while the teeth 116 of the leftmost undulate face 118 (in the orientation of FIG. 6B) include leading edge apices 226 to help with penetrating the teeth 116 laterally into an adjacent material, the teeth 116' of the rightmost undulate face 118' have no leading edge apices and therefore present a "blunter" surface to the ambient material. This may be desirable, for example, to avoid cutting into the ambient material with both undulate faces 118.

Figure 7A:
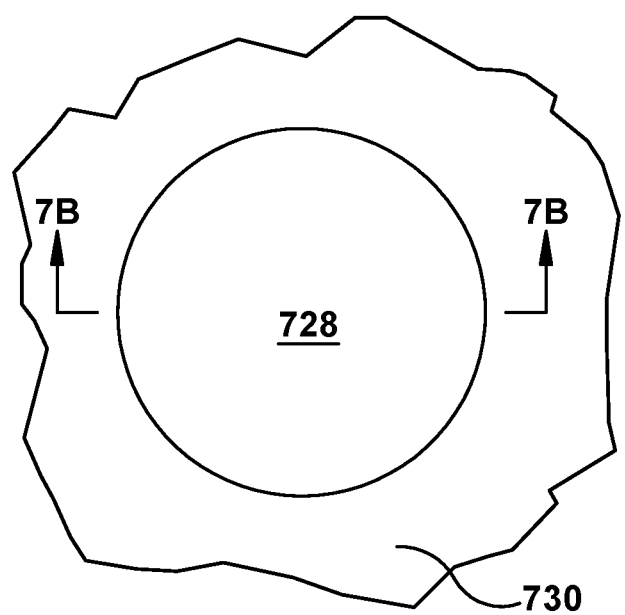
FIG. 7A is a top view of an example use environment for the present invention.
Figure 7B:
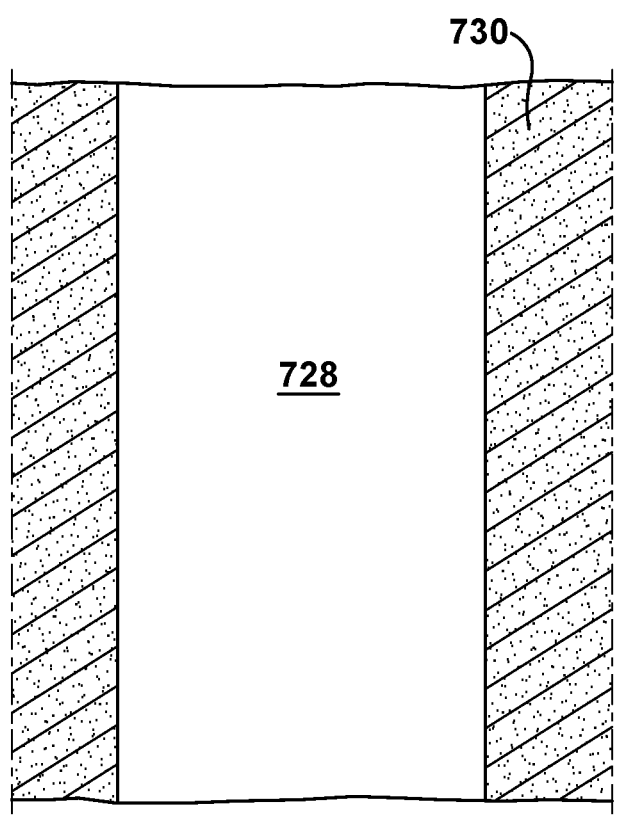
FIG. 7B is a cross-sectional view taken along line 7B-7B of FIG. 7A.

An example sequence of operation of the fastener 100 is shown pictorially in FIGS. 7A-15B. In FIGS. 7A and 7B, a longitudinally oriented pilot hole 728 is provided in a receiving substrate or receiving structure 730. The pilot hole 728 may be, for example, drilled into the receiving structure 730 or otherwise formed in any suitable manner. The receiving structure 730 may be of any suitable type and provided for any desired reason, though in the interest of discussion, the receiving structure is presumed to be a relatively hard and inflexible patient tissue, such as the bone tissue of a tibia or femur in an ACL replacement surgical setting.

In order for the receiving structure 730 to accommodate the fastener 100 as described herein, the pilot hole 728 must be transformed into a receiving aperture. An example of a suitable shaping tool 832 for refining and adjusting a substantially cylindrical pilot hole 728 is shown in FIG. 8. As can be seen in the exploded view of FIG. 8, the shaping tool 832 includes an elongate guiding rod 834 having a "female" dovetail-shaped guiding track 836. A guided chisel 838 includes a "male" dovetail-shaped guided rail 840 configured for mating engagement with the guiding track 836. The guided chisel 838 includes a shaping face 842 of any desired size, configuration, and sharpness.

The term "mate" is used herein to indicate a relationship between two separate structures which are joined or fitted together closely because they have similar three-dimensional shapes (e.g., a positive and a negative version of the same contour, respectively). Two structures in a "mated" relationship may include at least some space therebetween, or may even have a thin interposed structure (e.g., a cushion or membrane), but should be configured to fit substantially closely together at the mated interface. The guiding rod 834 may be mated with at least a portion of the guided chisel 838, or these structures may be spaced apart in any desired manner, and by any desired amount.

Figure 10A:
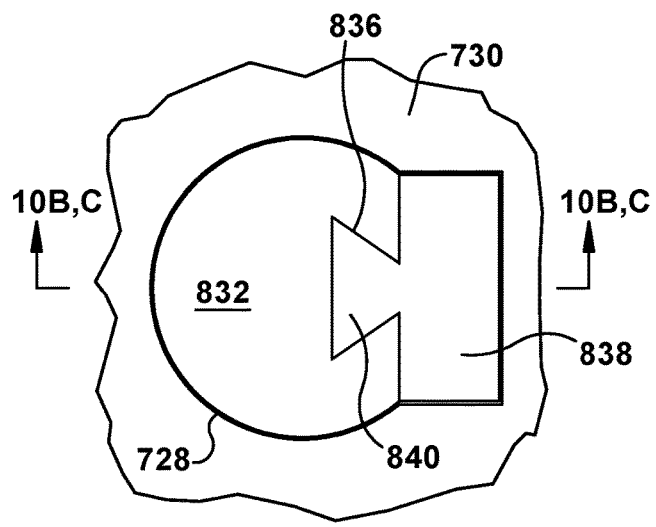
FIG. 10A is a top view of the tool of FIG. 8 in the use environment of FIG. 7A.
Figure 10B:
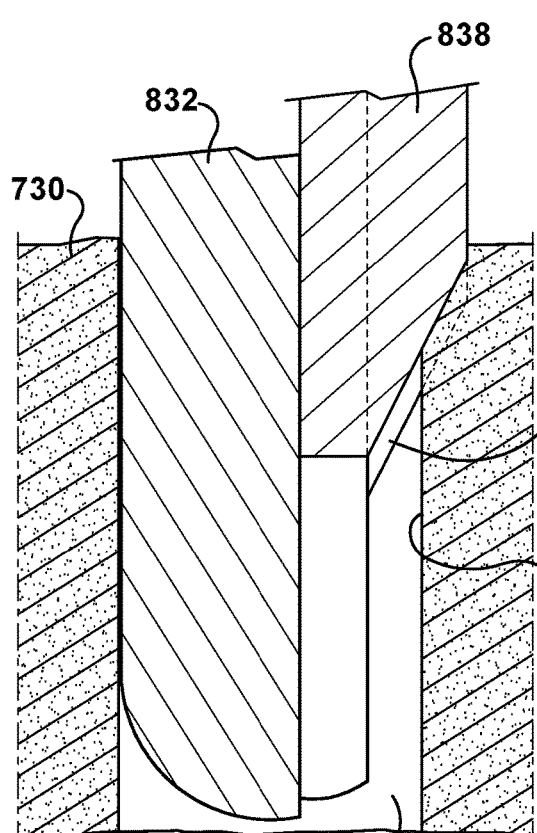
FIGS. 10B and 10C are cross-sectional views taken along line 10B,C-10B, C of FIG. 10A and depicting a sequence of use of the tool of FIG. 8.

In FIGS. 9A and 9B, the guiding rod 834 has been at least partially inserted longitudinally into the cylindrical pilot hole 728, with the guiding track 836 facing a desired, and possibly predetermined, direction (toward the right of the page, in the orientation of FIGS. 9A and 9B). In FIGS. 10A and 10B, the guided chisel 838 has been mated with the guiding rod 836 by insertion of at least a portion of the guided rail 840 into the guiding track 836. This mating can occur before, during, or after insertion of the guiding rod 834 into the pilot hole 728. The shaping face 842 comes into contact with, and optionally penetrates, the rightmost side (in the orientation of these Figures) of an interior wall 1044 of the pilot hole 728.

Figure 10C:
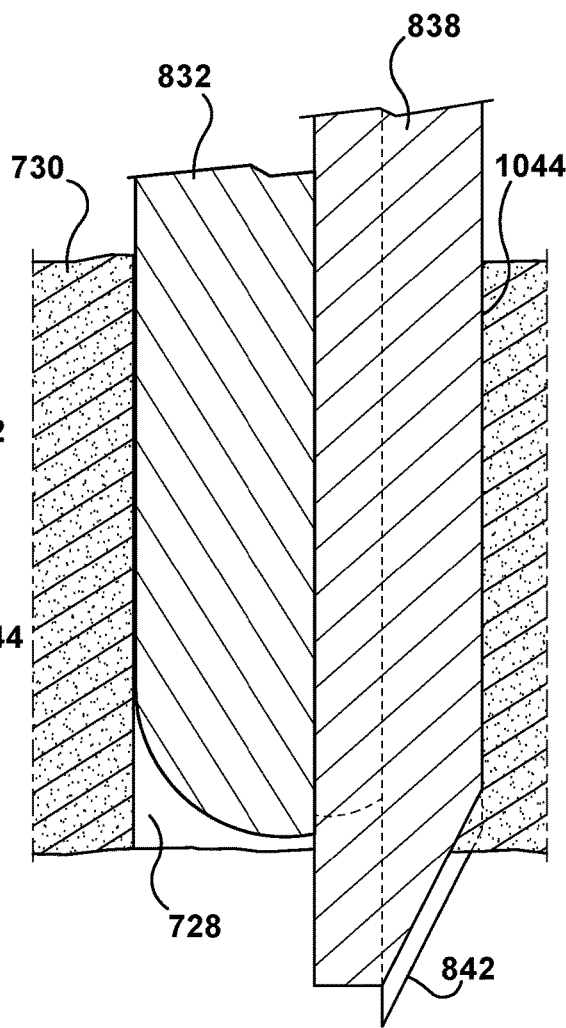

In the sequence of operation from FIG. 10B to FIG. 10C, the guiding rod 834 is maintained substantially in the same position within the pilot hole 728 while the guided chisel 838 is guided into the mass of the receiving structure 730 laterally adjacent to the pilot hole 728 through sliding engagement between the guiding track 836 of the guiding rod and the guided rail 840 of the guided chisel. It is likely that, for most applications of the present invention, a substantial degree of force (above a mere gravitational force upon the guided chisel 838) will be exerted upon one or both of the guiding rod 834 and the guided chisel to cause the motion shown from FIG. 10B to FIG. 10C.

As the guided chisel 838 travels longitudinally downward (in the orientation of FIGS. 10B and 10C) into the pilot hole 728, the shaping face 842 comes into penetrating contact with the interior wall 1044 of the pilot hole. Due at least partially to this penetrating contact and longitudinal motion, the shaping face 842 excavates the receiving structure 730 laterally adjacent to the pilot hole 728. "Excavate" here is intended to mean "create a cavity or hole in". This excavation may happen via cutting, digging out, or compression of the material making up the receiving structure 730, any other suitable material removal and/or rearrangement techniques, or any combination thereof. In some embodiments of the present invention, a relief channel (not shown) may be provided in the shaping tool 832 to facilitate removal from the pilot hole 728 of kerf or other loose material created/encountered during excavation of the receiving structure 730 laterally adjacent to the pilot hole.

Figure 11A:
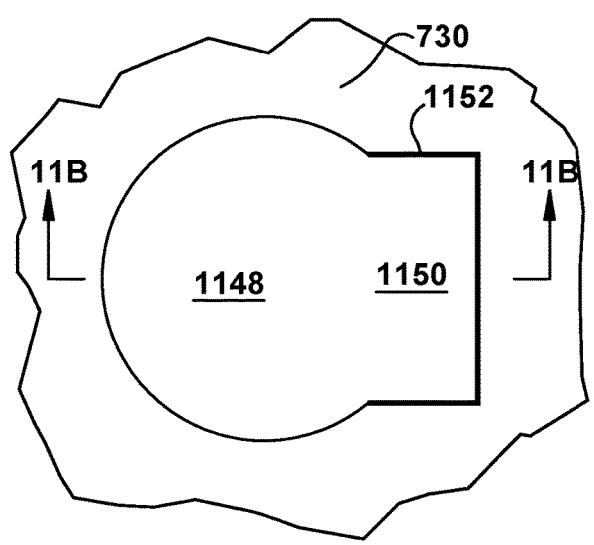
FIGS. 11A, 12A, 14A, and 15A are top views of the use environment of FIG. 7A depicting a sequence of operation of the embodiment of FIG. 1.
Figure 11B:
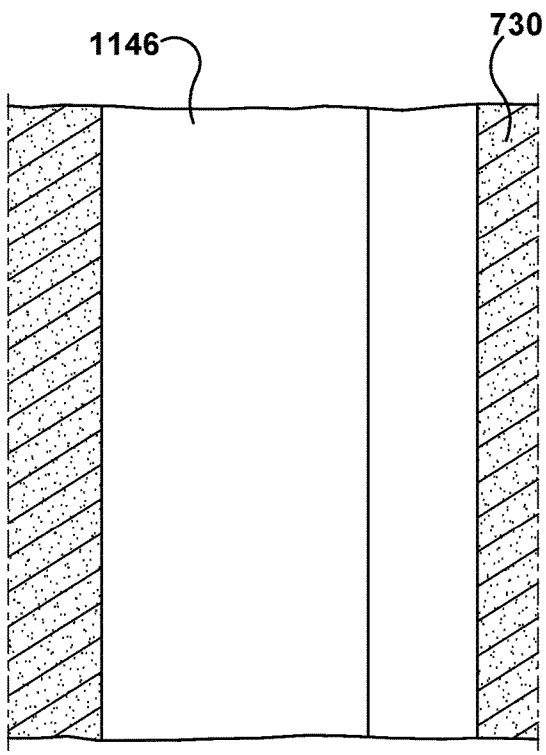
FIGS. 11B, 12B, 13B, 14B, and 15B are cross-sectional views taken, respectively, along line 11B-11B of FIG. 11A, 12B-12B of FIG. 12A, 13B-13B of FIG. 13A, 14B-14B of FIG. 14A, and 15B-15B of FIG. 15A.

Once the shaping tool 832 has been used as desired, the shaping tool may be removed from the receiving structure 730. As shown in FIGS. 11A and 11B, the shaping tool 832 is used to create, from the pilot hole 728, a receiving aperture 1146 which is rotationally asymmetrical and has a structure-receiving portion 1148 laterally adjacent to a fastener-receiving portion 1150.

Figure 12A:
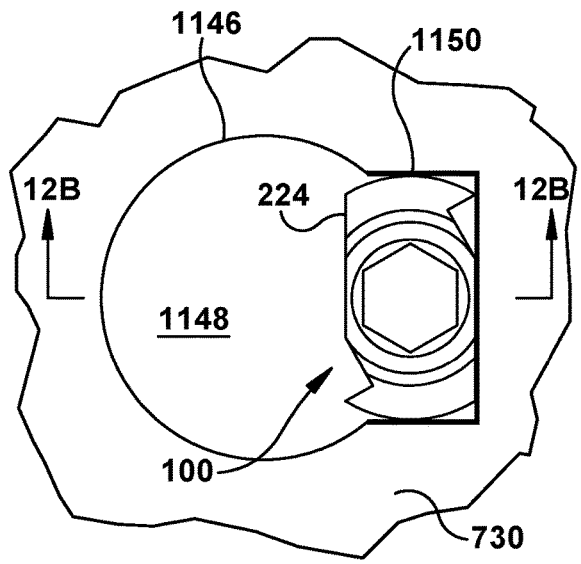
Figure 12B:
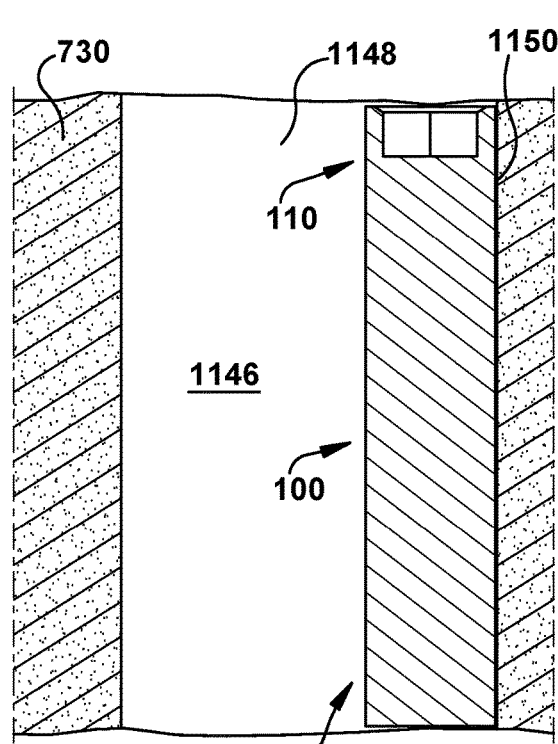

With reference to FIGS. 12A and 12B, the fastener tip end 112 may be inserted into the receiving aperture 1146, such as into a fastener-receiving portion 1150 thereof. The fastener 100 the can penetrate into the receiving aperture 1146 to a predetermined depth. Optionally, the fastener 100 may include a depth-stop feature (not shown), such as an increased-lateral-width fastener head end, which can be used to prevent insertion of the fastener deeper into the receiving aperture 1146 than desired.

As shown in heavy line in FIG. 11A, the fastener-receiving portion 1150 of the fastener aperture 1146 may have a laterally-oriented footprint 1152 which surrounds a majority of the fastener perimeter 224. For many use environments of the present invention, it will be desirable to have at least some, if not all, of the undulate faces 118 of the fastener 100 surrounded by the fastener-receiving portion 1150 of the fastener aperture 1146, such that a flat face 120 of the fastener 100 is exposed or presented to the structure-receiving portion 1148 of the receiving aperture when the fastener is in a first alignment, as shown in FIGS. 12A and 12B.

Figure 13A:
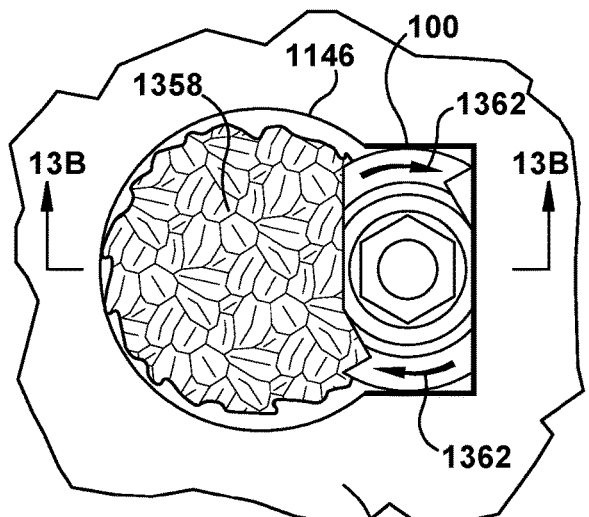
FIG. 13A is a top view of the use environment of FIG. 7A depicting an alternate step of the sequence of operation of the embodiment of FIG. 1.
Figure 14A:
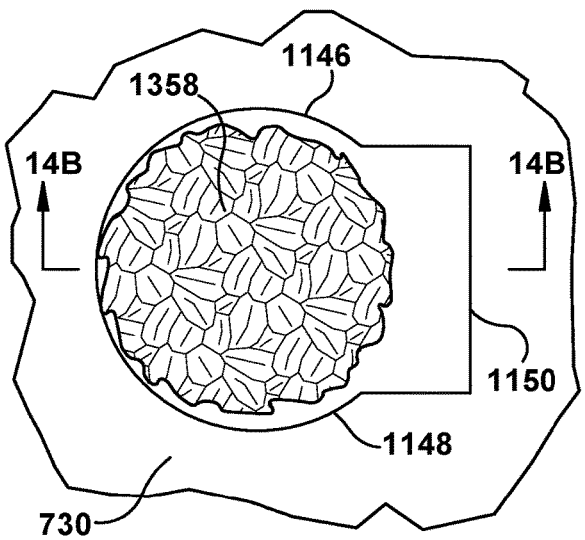
Figure 13B:
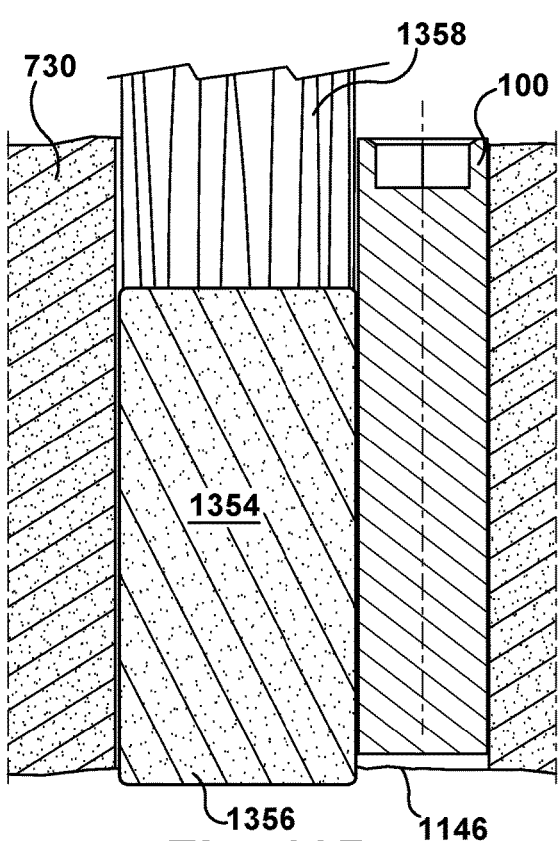
Figure 14B:
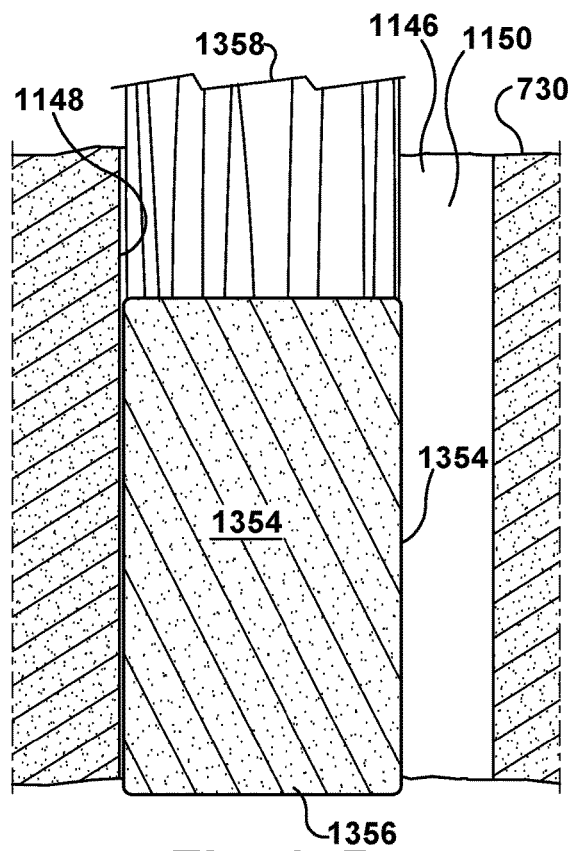

Regardless of the position or exposure of the fastener 100, however, the fastener may be retained in the receiving aperture 1146 in the first alignment while, as shown in FIGS. 13A and 13B, an anchored structure 1354 is at least partially inserted into the receiving aperture, laterally adjacent to the fastener. In the ACL replacement being used as an example herein, the anchored structure 1354 is a relatively rigid bone block 1356 (dimensioned for insertion into the receiving aperture 1146) which is attached to a relatively soft/flexible graft ligament 1358. The graft ligament 1258 may have a first graft end 1360 which is directly connected to the bone block 1356 and a second graft end (not shown) which also may be connected to a respective bone block (not shown) for anchoring elsewhere during the ACL replacement, optionally through the use of a second receiving aperture and a second fastener (not shown).

As another option for achieving the physical arrangement of structures shown in FIGS. 13A and 13B, the anchored structure 1354 could be inserted into the structure-receiving portion 1148 of the receiving aperture 1146 before the fastener 100 is inserted into the fastener-receiving portion 1150 of the receiving aperture.

Regardless of how the receiving structure 730, anchored structure 1354, and fastener 100 achieve their relative positions in the "ready to use" arrangement of FIGS. 13A and 13B with the fastener in the first alignment, the fastener 100 may be manipulated by a user at any desired time and in any desired manner to rotate substantially about the longitudinal axis 104 as shown by rotation arrows 1362 of FIG. 13A, which is clockwise, in the orientation of FIG. 13A.

Figure 15A:
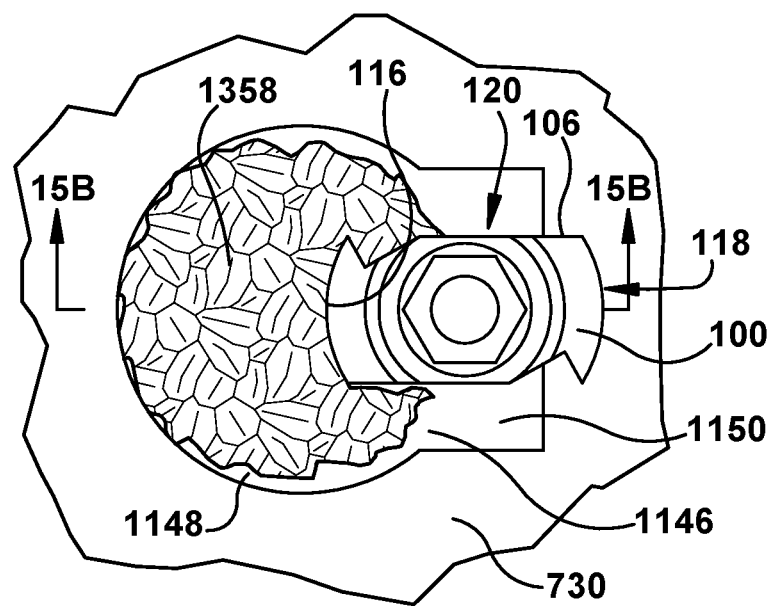
Figure 15B:
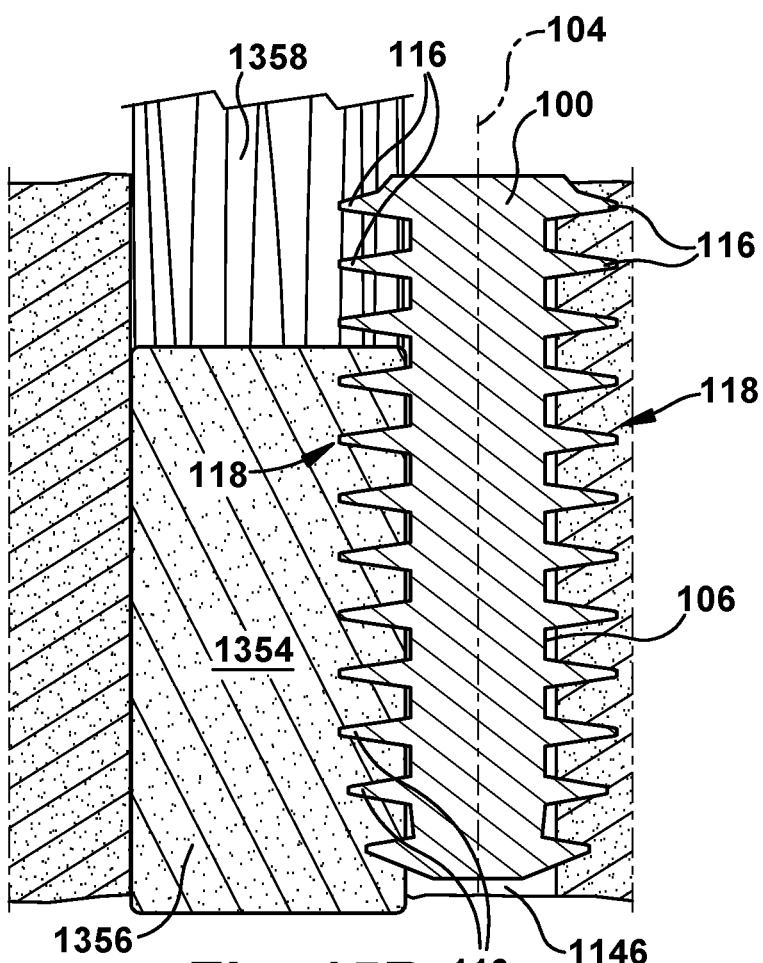

Through rotation of the fastener 100, the arrangement shown in FIGS. 15A and 15B may be achieved, wherein the fastener is in a second alignment. Here, the fastener has been rotated substantially ninety degrees about the longitudinal axis 104 within the receiving aperture 1146, into the second alignment. Due to rotation of the fastener 100 into the second alignment, at least one tooth 116 has been driven laterally into the receiving structure 730 from the receiving aperture 1146 (in other words, into the rightmost portion of the receiving structure 730, in the orientation of FIG. 15B). Also due to rotation of the fastener 100 into the second alignment, at least one tooth 116 has been driven laterally into the anchored structure 1354 (in other words, into the rightmost portion of the bone block 1356, in the orientation of FIG. 15B)—which may have occurred concurrently with driving of the teeth laterally into the receiving structure 730. The teeth 116 driven laterally into the receiving structure 730 are arranged upon (associated with) a different undulate face 118 of the fastener 100 from the teeth 116 driven laterally into the anchored structure 1354.

When the fastener 100 is in the second alignment, as shown in FIGS. 15A-15B, the user may wish to have a different arrangement of teeth 116 upon the fastener shell 106 than that shown. For example, it may be desirable to have different—or no—teeth 116 that are laterally driven into a graft ligament 1358 portion of the anchored structure 1354, particularly if the graft ligament portion is more sensitive to damage from laterally-oriented tooth contact than is the bone block 1356 portion. With reference back to the example tooth configurations of FIGS. 3-6B, one of ordinary skill in the art could provide a fastener for a particular use environment having a plurality of teeth 116 with any desired configuration, shape, size, cross-sectional profile, thickness, material, or other physical property, and the provided teeth need not match each or any other tooth in any respect.

Regardless of how the fastener 100 is moved from the "insertion" first alignment to the "gripping" second alignment, the fastener may be maintained within the receiving aperture 1146 via at least one tooth 116—of any desired type or configuration—driven laterally into at least one of the receiving structure 730 and the anchored structure 1354, to resist longitudinal movement of the fastener (and optionally the anchored structure) with respect to the receiving structure 730. In this manner, the anchored structure 1354 and/or fastener 100 can be secured in the receiving structure 730 as desired, for any suitable securement task.

Figure 16:
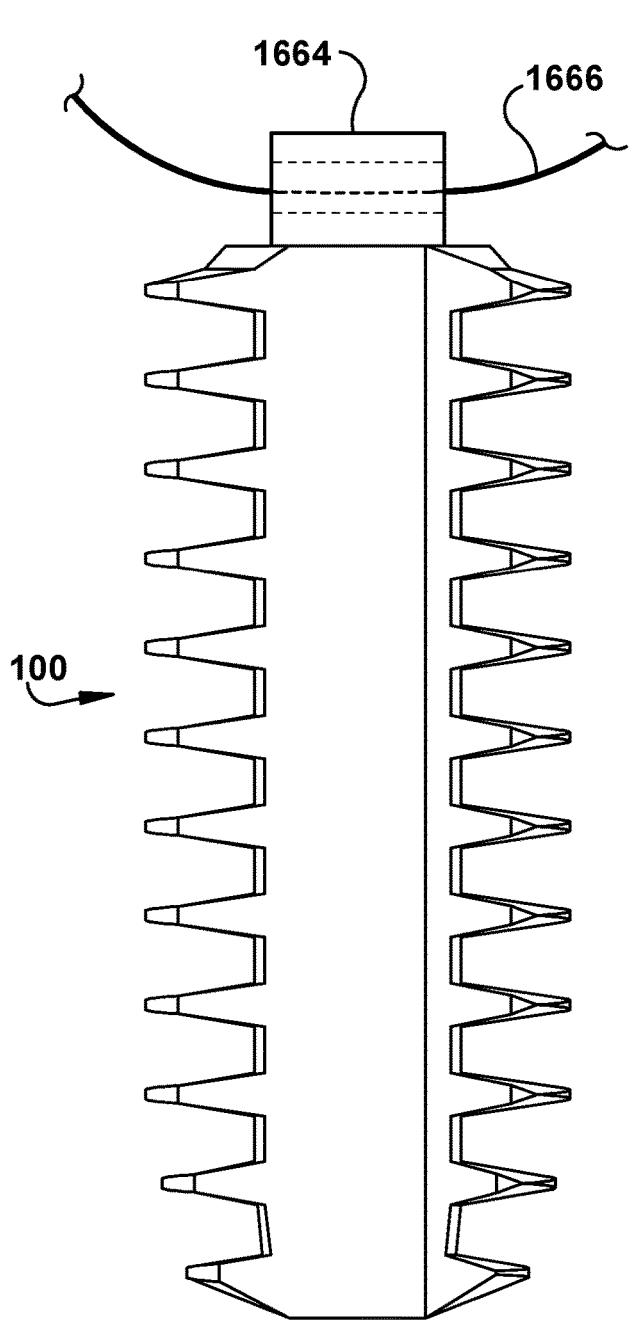
FIG. 16 is a front view of the embodiment of FIG. 1 in an alternate configuration.
Figure 17:
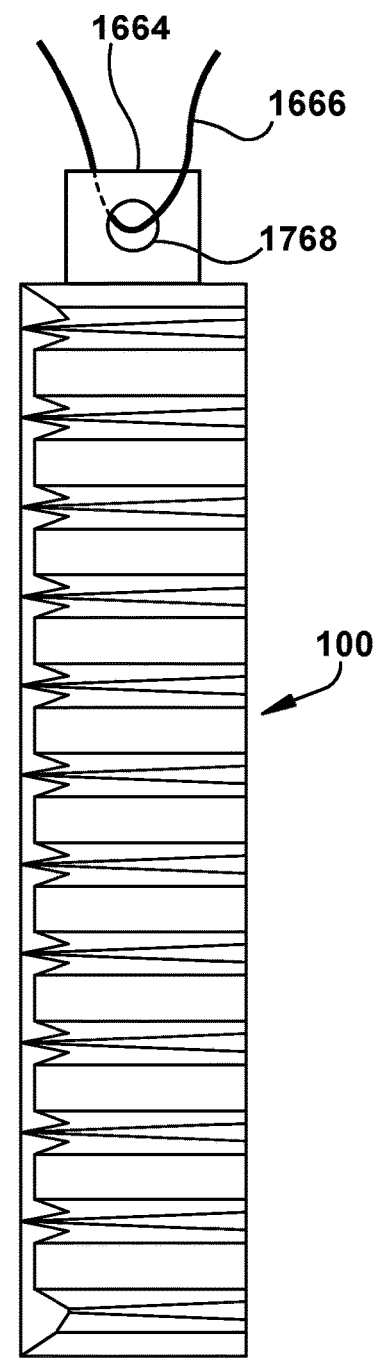
FIG. 17 is a side view of the embodiment of FIG. 1 in the alternate configuration of FIG. 16.

The fastener 100 could include one or more features which assist in performing a particular securement task. For example, and as shown in FIGS. 16 and 17, a suture lug 1664, configured to retain a suture thread 1666, may be provided. In FIGS. 16 and 17, the suture thread 1666 passes through a suture aperture 1768 in the suture lug 1664 and thereby the suture thread may be anchored to a receiving structure 730 while allowing sliding of the suture thread within the suture aperture 1768. However, it is also contemplated that the suture thread 1666 could be rigidly or non-movably connected to the suture lug 1664 in any suitable manner, if desired.

The sequence of FIGS. 18A-20C depicts the installation of a fastener 100 which may be used for a suture anchoring or other task which does not include the engagement/connection of an anchored structure (omitted from these Figures) with a receiving structure 730 through use of a fastener. The sequence of operation in FIGS. 18A-20C is similar to that described above with reference to FIGS. 7A-15B, and similar structures and functions to those discussed above will not be specifically discussed again here.

Figure 18A:
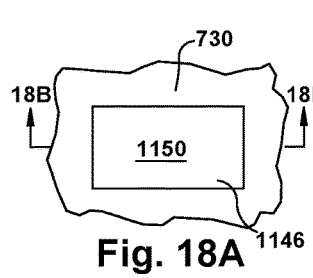
Figure 18B:
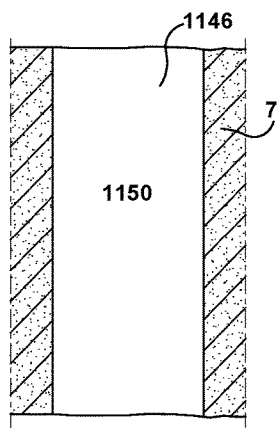

As seen in FIGS. 18A and 18B, the receiving aperture 1146 includes only a fastener-receiving portion 1150, and may be formed in any suitable manner. For most applications of the present invention, the footprint 1152 of the receiving aperture 1146 when no anchored structure is present will hew rather closely to the fastener perimeter 224. That is, the receiving aperture 1146 in a situation such as that of FIGS. 18A-20C will be similar in shape and size to the fastener perimeter 224 such that the fastener 100 can be inserted in a desired manner without undue effort or excessive damage to the receiving structure 730 or the fastener, but so that the teeth 116 will find ample purchase, when the fastener is in in the second alignment, to secure the fastener as desired.

Figure 20A:
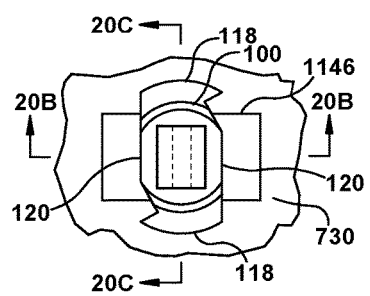
FIGS. 18A, 19A, and 20A are top views of an example use environment depicting a sequence of operation of the embodiment of FIG. 1 in the alternate configuration of FIG. 16.
Figure 19A:
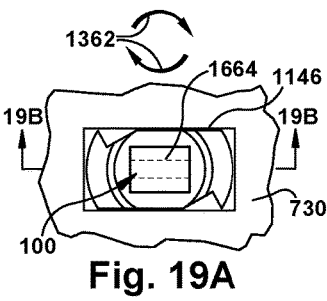
Figure 19B:
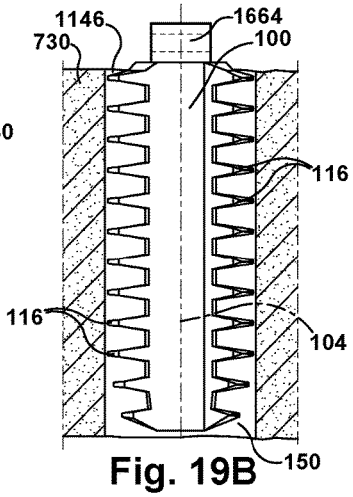

The receiving aperture 1146 may be formed in any desired manner, and then, as in FIGS. 19B and 19C, the fastener 100 may be inserted into the receiving aperture in the first alignment. The fastener 100 may then be rotated about the longitudinal axis 104 thereof, in the clockwise direction of the rotation arrows 1362, into the second alignment position shown in FIGS. 20A, 20B, and 20C. FIGS. 20A and 20C show how the teeth 116 of the fastener 100 have been driven laterally into the receiving structure 730 to resist pullout and maintain the fastener in the second alignment for as long as desired.

Figure 20B:
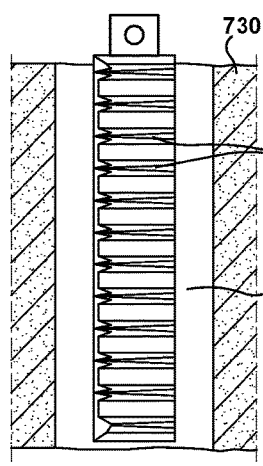
FIGS. 18B, 19B, 20B, and 20C are cross-sectional views taken, respectively, along line 18B-18B of FIG. 18A, 19B-19B of FIG. 12A, 20B-20B of FIG. 20A, and 20C-20C of FIG. 20A.
Figure 20C:
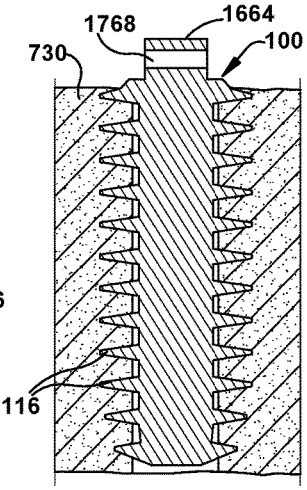

As can be seen in FIGS. 20A and 20B, rotation of the fastener 100 can leave some empty space within the receiving aperture 1146, laterally adjacent to the flat faces 120 of the fastener. Optionally, some filler material such as, but not limited to, bone graft, bone cement, or any other desired material, may be used to fill the receiving aperture 1146 and may be helpful in securing the fastener 100 within the receiving aperture. It is also contemplated that the teeth 116, flat faces 120, or any other portion(s) of the fastener shell 106, regardless of use environment, could include an ingrowth encouragement feature such as, but not limited to, a coating of natural or artificial bone growth factor, a texturized (peened or gritted) surface, or any other desired feature.

In the above description, the fastener 100 is characterized as being rotated from the first to the second alignment about the longitudinal axis 104. While the present invention is agnostic and apathetic as to how that rotation occurs, it is contemplated that, for most applications of the present invention, rotary force will be transmitted from a manipulation tool to the fastener body 102 via a tool-engaging feature 114 on the fastener head end 110. Any desired type of tool-engaging feature 114 and corresponding manipulation tool may be used with the present invention, such as, but not limited to, a manipulation tool which is an Allen wrench, Philips screwdriver, slotted screwdriver, TORX™ wrench, Robertson wrench, inside hex wrench, or any other suitable manipulation tool or combination thereof.

Figure 21:
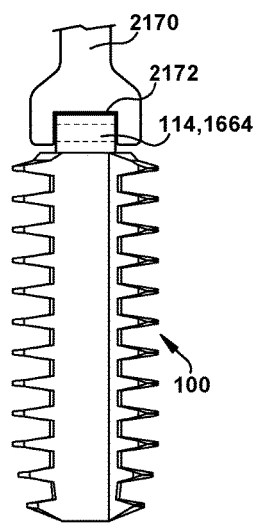
FIG. 21 is a front view of the embodiment of FIG. 1 in an alternate configuration.
Figure 22:
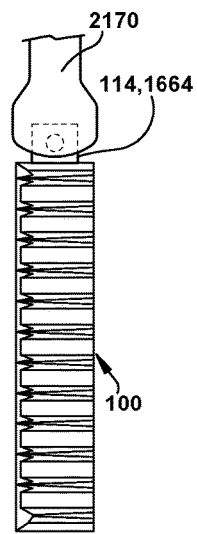
FIG. 22 is a side view of the embodiment of FIG. 1 in the alternate configuration of FIG. 21.

As shown in FIGS. 21-22, the fastener 100 of FIGS. 18A-20C has a suture lug 1664 which also can be used as a tool-engaging feature 114 and which protrudes from the fastener head end 110. The tool-engaging feature 114 of FIGS. 21-22 also includes an anchor feature (the suture aperture 1768) which connects to a structure (the suture thread 1666) being anchored by the fastener 100. In the embodiment of FIGS. 21-22, a lug wrench 2170 includes a lug acceptor 2172 that is configured to substantially mate with the suture lug 1664. Rotation of the lug wrench 2170 is then transmitted through the lug acceptor 2172 to the suture lug 1664 to rotate the fastener 100.

Figure 23A:
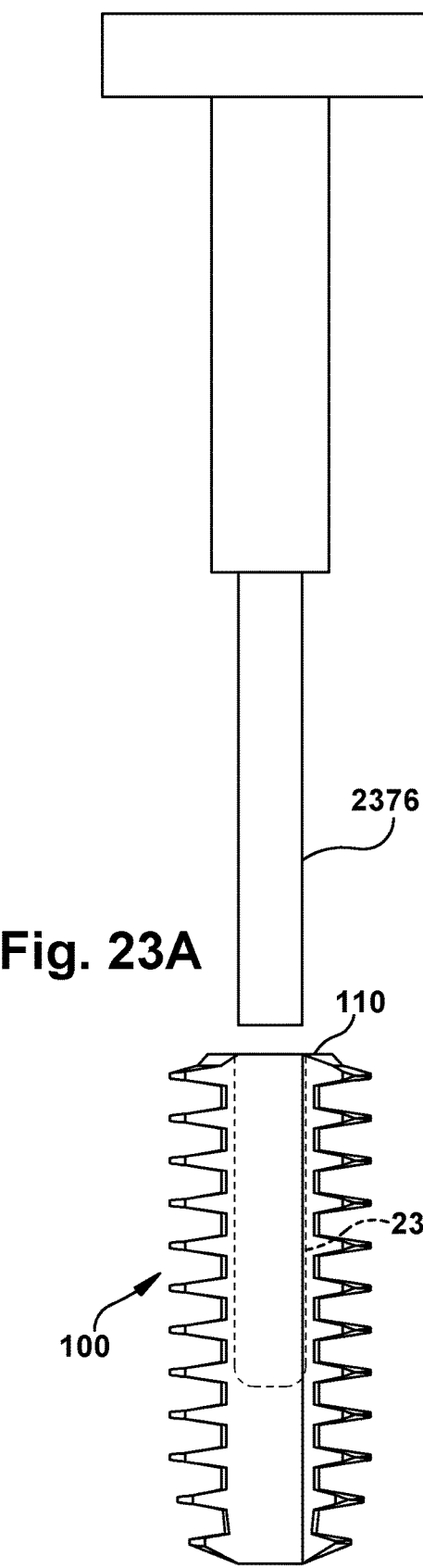
FIGS. 23A-23B depict a sequence of operation of the embodiment of FIG. 1 in an alternate configuration.
Figure 23C:
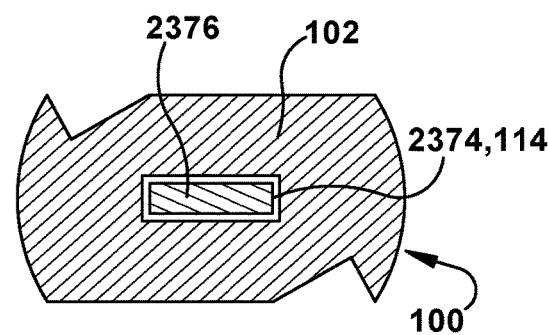
FIG. 23C is a cross-sectional view taken along line 23C-23C of FIG. 23A.
Figure 23B:
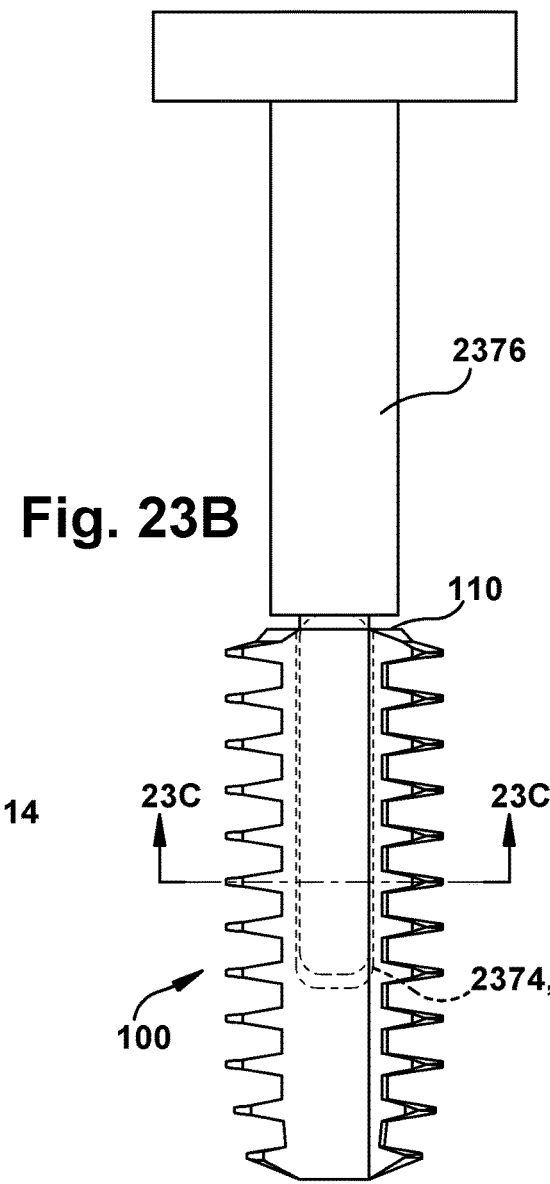

As another example of a suitable means for rotating the fastener, FIGS. 23A-23C depict a fastener 100 having a relatively deep center void 2374 recessed into the fastener head end 110 and extending into the fastener body 102 as a tool-engaging feature 114. The center void 2374 is configured to accept at least a portion of a corresponding void wrench 2376 in a male-to-female type manner and the center void and void wrench are configured such that rotation of the void wrench is transmitted to the fastener body 102 via the center void (i.e., the void wrench does not just spin in place within the center void). The arrangement shown in FIGS. 23A-23C is similar in tool-engaging principle to the hex-head tool-engaging feature 114 shown in FIGS. 1-15B. The FIGS. 23A-23C arrangement, however, may be especially desirable when an adsorbable, absorbable, or other "deteriorating" material—which is generally rather brittle—is used to make the fastener 100. Since the void wrench 2376 is inserted a relatively long distance into the fastener body 102, the void wrench can help to strengthen and reinforce the structure of a dissolving or absorbable fastener 100 to avoid unwanted damage to the fastener 100 due to the rotation forces.

The undulate or flat quality of a face might not be present in each and every dimension and portion of that face, but one of ordinary skill in the art, upon viewing a face of a fastener shell 106, will be able to readily determine whether the face is undulate or flat, for the purposes of the present invention. Additionally, the boundaries or borders between laterally adjacent faces might not be clearly drawn or delineated in all embodiments of the present invention, but, again, one of ordinary skill in the art will be able to at least broadly identify and differentiate portions of the fastener shell 106 that are undulate or flat.

While the undulate faces 118 and flat faces 120 discussed herein all have relatively large and similar lateral widths (i.e., the dimensions of each that combine to form the fastener perimeter 224), it is contemplated that the undulate faces and flat faces could have any desired width, down to and including a near-zero width. In other words, the profile 322 may be formed as a quasi-linear construct as a longitudinally extending edge of the fastener shell 106 at a lateral intersection of two flat faces 120.

The pilot hole 728 and/or receiving aperture 1146 may each be created in any desired manner, using any desired manual, automatic, and/or semi-automatic material removal/shaping tools. Optionally, the receiving aperture 1146 may be formed directly in the receiving structure 730, with no pilot hole 728 previously provided.

The shaping tool 832 could use any suitable structures for placement and guiding of the guided chisel 838 with respect to the guiding rod 834. For example, the "male" and "female" portions of the interlocking features of the guiding rod 834 and guided chisel 838 could be reversed from that shown in the Figures. Any other desired (non-dovetail) relatively shaped structures, whether or not interlocking mating actually occurs, could be used for placement and guiding of the guided chisel 838 with respect to the guiding rod 834.

It is contemplated that movement of the fastener 100 from the first alignment to the second alignment will occur via rotation of the fastener through about ninety degrees, or a quarter-turn, about the longitudinal axis 104 of the fastener—this rotation will generally be oriented clockwise to comport with mechanical convention. The rotation will generally be restricted to this quarter-turn movement to provide adequate securement of the fastener 100 while avoiding damage to the receiving structure 730 and/or anchored structure 1354 due to repeated or excessive "biting" or penetrating of the teeth 116 thereinto and possible overall weakening of the connected structures. However, in a particular application of the present invention, it may be desirable for the fastener 100 to be rotated further than ninety degrees, including one or more full three hundred sixty degree rotations, during actuation of the fastener from the first alignment into the second alignment, and one of ordinary skill in the art can readily provide a suitably designed fastener, receiving structure 730, and/or anchored structure 1354 for such a use environment.

To remove the fastener 100 if/when it is no longer desired to be in the second alignment in the receiving structure 730, the fastener could be caused to rotate back from the second alignment to the first alignment, such as by a rotation of about ninety degrees about the longitudinal axis 104 in the opposite direction (e.g., counterclockwise) from the installation rotation direction. Any suitable tool, including the installation tool, could be used for removal. The fastener 100 can then be pulled longitudinally out of the receiving aperture 1146, optionally with the aid of a removal tool that includes any suitable grasping feature to aid in pulling the fastener from the receiving structure 730. As another option, the fastener 100 could be rotated further than ninety degrees, including one or more full three hundred sixty degree rotations, to "back out" of the receiving aperture 1146 similarly to removal of a standard cylindrical screw/bolt.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the fastener 100 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single unitary or monolithic piece or made up of separate sub-components, with either of these formations involving any suitable stock or bespoke components and/or any suitable material or combinations of materials; however, the chosen material(s) for the fastener 100 should be biocompatible for many applications of the present invention and may be adsorbable or absorbable to deteriorate or ingrow with the receiving structure 730 over time. The mating relationships formed between the described structures need not keep the entirety of each of the "mating" surfaces in direct contact with each other but could include spacers or holdaways for partial direct contact, a liner or other intermediate member for indirect contact, or could even be approximated with intervening space remaining therebetween and no contact. Some degree of lateral translation movement may also occur during rotation of the fastener 100 about the longitudinal axis 104. The rotation of the fastener 100 about the longitudinal axis 104 could occur in the clockwise direction of the rotation arrows 1362 or in a counterclockwise direction, contrary to the rotation arrows. The fastener body 102 may include a longitudinally-oriented central bore (not shown) through an entire length thereof. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A system of installing a fastener into a solid patient tissue at a target side, the fastener including an elongate fastener body defining a longitudinal axis substantially central thereto, the fastener body having a continuous outer fastener shell laterally surrounding the longitudinal axis, the fastener shell longitudinally separating a fastener head end and a fastener tip end, a tool-engaging feature on the fastener head end, and a plurality of teeth located on the fastener shell and extending substantially laterally outward from the longitudinal axis, the system including:
   a circular drill for producing a substantially cylindrical pilot hole extending longitudinally into the solid patient tissue at the target site; and
   a shaping tool including an elongate guiding rod and an elongate guided chisel for selective mating engagement with the guiding rod, the guiding rod being configured for insertion into the pilot hole, and the guided chisel being configured for lateral penetration into an interior wall of the pilot hole under longitudinal motion guided by the guiding rod;
   wherein the lateral penetration of the guided chisel into the interior wall of the pilot hole excavates a receiving structure laterally adjacent to the pilot hole, the receiving structure and pilot hole comprising a rotationally asymmetrical receiving aperture configured to receive at least a portion of the fastener body thereinto.

2. The system of claim 1, wherein the guiding rod and guided chisel selectively mate with each other via a male-to-female dovetail mechanism.

3. The system of claim 2, wherein the guiding rod includes a dovetail guiding track and the guided chisel includes a dovetail guided rail.

4. The system of claim 1, wherein the shaping tool includes a relief channel for removal of loose material created or encountered during excavation of the receiving structure.

5. The system of claim 1, including a manipulation tool configured for engagement with a tool-engaging feature on the fastener head end, the manipulation tool being manipulable to transmit rotary force to the fastener body to rotate the fastener about the longitudinal axis within at least a portion of the receiving aperture.

\* \* \* \* \*